United States Patent [19]

Johnson, Jr.

[11] Patent Number: 4,628,945
[45] Date of Patent: Dec. 16, 1986

[54] INFLATABLE ANKLE BRACE WITH POROUS COMPRESSIBLE FILLER

[76] Inventor: Glenn W. Johnson, Jr., 10 Friar Tuck Cir., Summit, N.J. 07901

[21] Appl. No.: 694,700

[22] Filed: Jan. 25, 1985

[51] Int. Cl.$^4$ .............................................. A61F 3/00
[52] U.S. Cl. ............................... 128/80 H; 128/89 R; 128/DIG. 20
[58] Field of Search ............... 128/80 R, 80 C, 80 D, 128/80 F, 80 H, 80 E, 83, 84 R, 85, 87 R, 88, 89 R, 165, 166, 166.5, DIG. 20, 462, 118; 2/DIG. 3, DIG. 7, DIG. 10, 413, 22–24

[56] References Cited

U.S. PATENT DOCUMENTS

| | | | |
|---|---|---|---|
| 1,602,454 | 10/1926 | Riddell | 2/23 |
| 2,573,698 | 11/1951 | Ellery | 128/80 E |
| 2,694,395 | 11/1954 | Brown | 128/118 X |
| 4,077,400 | 3/1978 | Harrigan | 128/24 R |
| 4,280,489 | 7/1981 | Johnson, Jr. | 128/89 R X |
| 4,289,122 | 9/1981 | Mason et al. | 128/80 H X |
| 4,497,070 | 2/1985 | Cho | 2/22 |
| 4,505,269 | 3/1985 | Davies et al. | 128/87 R |
| 4,517,968 | 5/1985 | Greene et al. | 128/166 X |

FOREIGN PATENT DOCUMENTS

| | | | |
|---|---|---|---|
| 48442 | 3/1982 | European Pat. Off. | 2/413 |
| 41667 | 12/1932 | France | 128/118 |
| 947772 | 1/1964 | United Kingdom | 2/413 |

*Primary Examiner*—Clifford D. Crowder
*Attorney, Agent, or Firm*—S. Michael Bender

[57] ABSTRACT

Improved orthepedic apparatus in the form of a generally U-shaped stirrup member having a base portion and a pair of opposed sidewall portions hinged to the base portion. A pair of air-inflatable liners or airbags are disposed interiorly of the stirrup member in a juxtaposed, substantially coextensive relation to the sidewall portions, respectively. Fastener straps are provided to maintain the sidewall portions of the stirrup snuggly fitted about the lower extremity. A resilient, compressible filler member, porous and permeable to air, is disposed interiorly of each airbag to serve the dual function of pre-inflating the airbag prior to the stirrup member being fitted about the lower extremity, and simultaneously providing a cushioning member between the stirrup member and the lower extremity. Value means are also provided on each airbag to facilitate further inflation of that airbag or reduction of internal air pressure at elevated altitudes.

9 Claims, 4 Drawing Figures

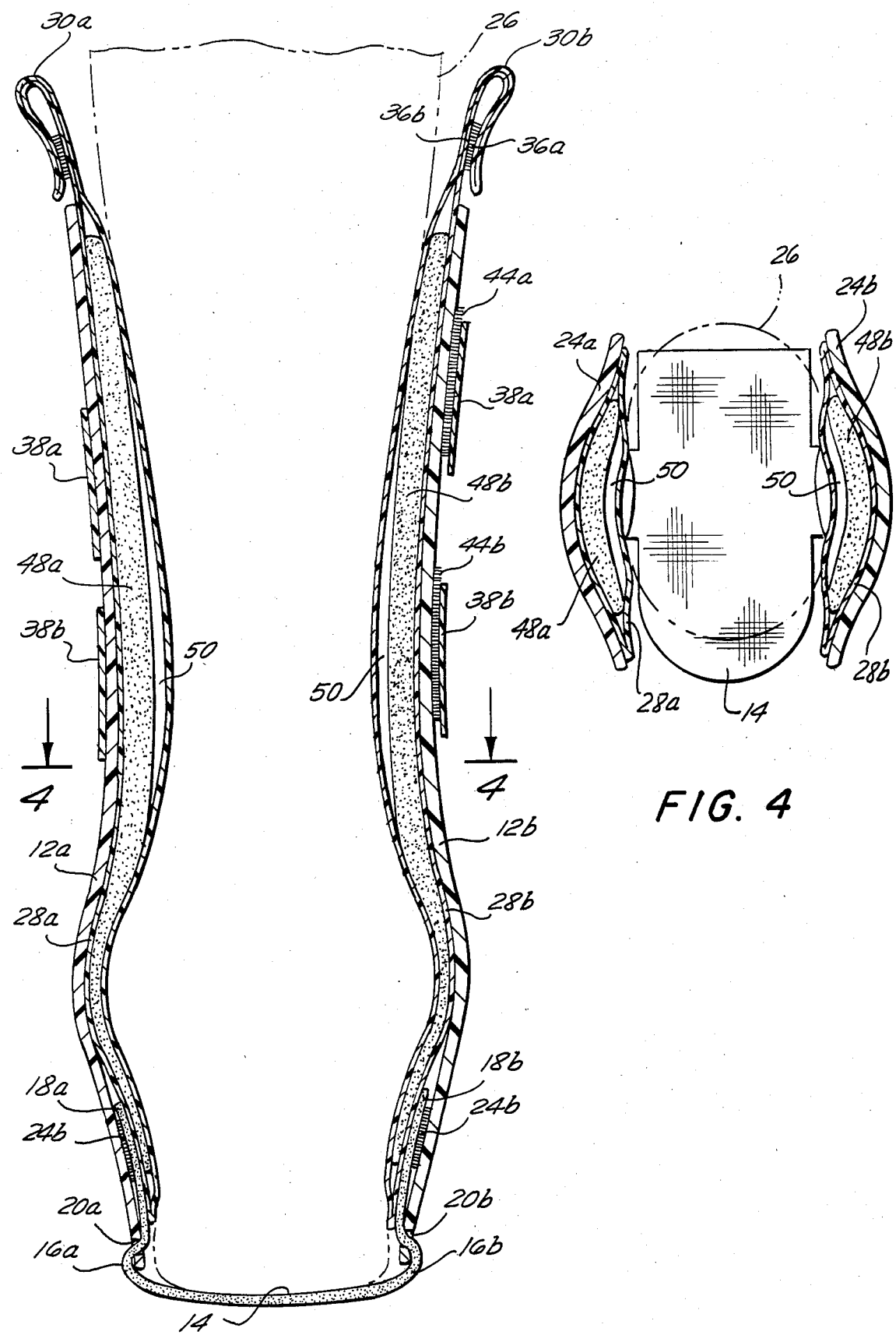

INFLATABLE ANKLE BRACE WITH POROUS COMPRESSIBLE FILLER

The present invention relates generally to new and useful improvements in ankle braces, and more particularly, to an improved form of pneumatic ankle brace featuring one or more inflatable liners or supporting cushions.

In my prior U.S. Pat. No. 4,280,489, entitled "Ankle Brace", there is fully described an orthopedic apparatus comprising a U-shaped stirrup member, a pair of opposed, inflatable liners or airbags disposed within the stirrup member in coextensive relation to the upstanding side walls thereof, and strap fastening means for maintaining the stirrup member sidewalls in engagement with the lower leg whereby subsequent inflation of the airbags will produce a firm supporting cushion of pressurized air in the voids between the irregular contours of the lower leg and the inside surfaces of the stirrup member side walls. By this arrangement, the ankle is stabilized against eversion and inversion without restricting planto flexion and dorsiflexion, and since the ankle brace may be worn with a conventional shoe, ambulatory functionality and/or the use of permitted exercises are encouraged thereby facilitating recovery from various injuries to the lower extremity e.g., ankle sprains.

While ankle braces incorporating the inventions disclosed and claimed in my prior U.S. Pat. No. 4,280,489, marketed by AIRCAST, INC., Summit, N.J., under the registered trademark AIR-STIRRUP, have enjoyed immediate and widespread commercial success, these devices still suffer from a disadvantage. It was found that in certain cases, despite proper inflation of the airbags disposed between the lower extremity and the inner sidewall surfaces of the stirrup member, the protruding boney portions of the ankle (e.g., in the region of the malleolus where the extent of airbag expansion typically is at a minimum) tend to locally compress the inflated airbag causing the pressurized air in the compressed portion of the airbag to be displaced, usually to the region above the malleolus where larger voids exist between the lower extremity and the sidewalls of the stirrup. Inasmuch as the locally compressed airbag material is relatively thin and incompressible, it is insufficient to provide adequate cushioning effect, consequently, enabling the protruding portion of the ankle to rub up against or abut the hard inner surface of the stirrup sidewall resulting in discomfort to the wearer.

Accordingly, it is a primary object of the present invention to provide an improved pneumatic ankle brace having means for overcoming the aforementioned disadvantage.

Toward the accomplishment of this and additional objectives and advantages, the present invention briefly described comprises a generally U-shaped stirrup member having a base portion and a pair of opposed sidewall portions hinged to the base portion. A pair of air-inflatable liners or airbags are disposed interiorly of the stirrup member in a juxtaposed substantially coextensive relation to the sidewall portions, respectively. Fastener straps are provided to maintain the sidewall portions of the stirrup snuggly fitted about the lower extremity. A resilient, compressible filler member, porous and permeable to air, is disposed interiorly of each airbag to serve the dual function of pre-inflating the airbag prior to the stirrup member being fitted about the lower extremity, and simulatneously, providing a cushioning member between the stirrup member and the lower extremity. Valve means are also provided on each airbag to facilitate further inflation of that airbag or reduction of internal air pressure at elevated altitudes.

The foregoing and still further features and advantages of the present invention as well as a more complete understanding thereof will be made apparent from a study of the following detailed description of the invention in connection with the accompanying drawings wherein:

FIG. 3 is a sectional view in elevation taken along line 3—3 of FIG. 2; and

FIG. 4 is a sectional plan view taken along line 4—4 of FIG. 3.

Figure 1:
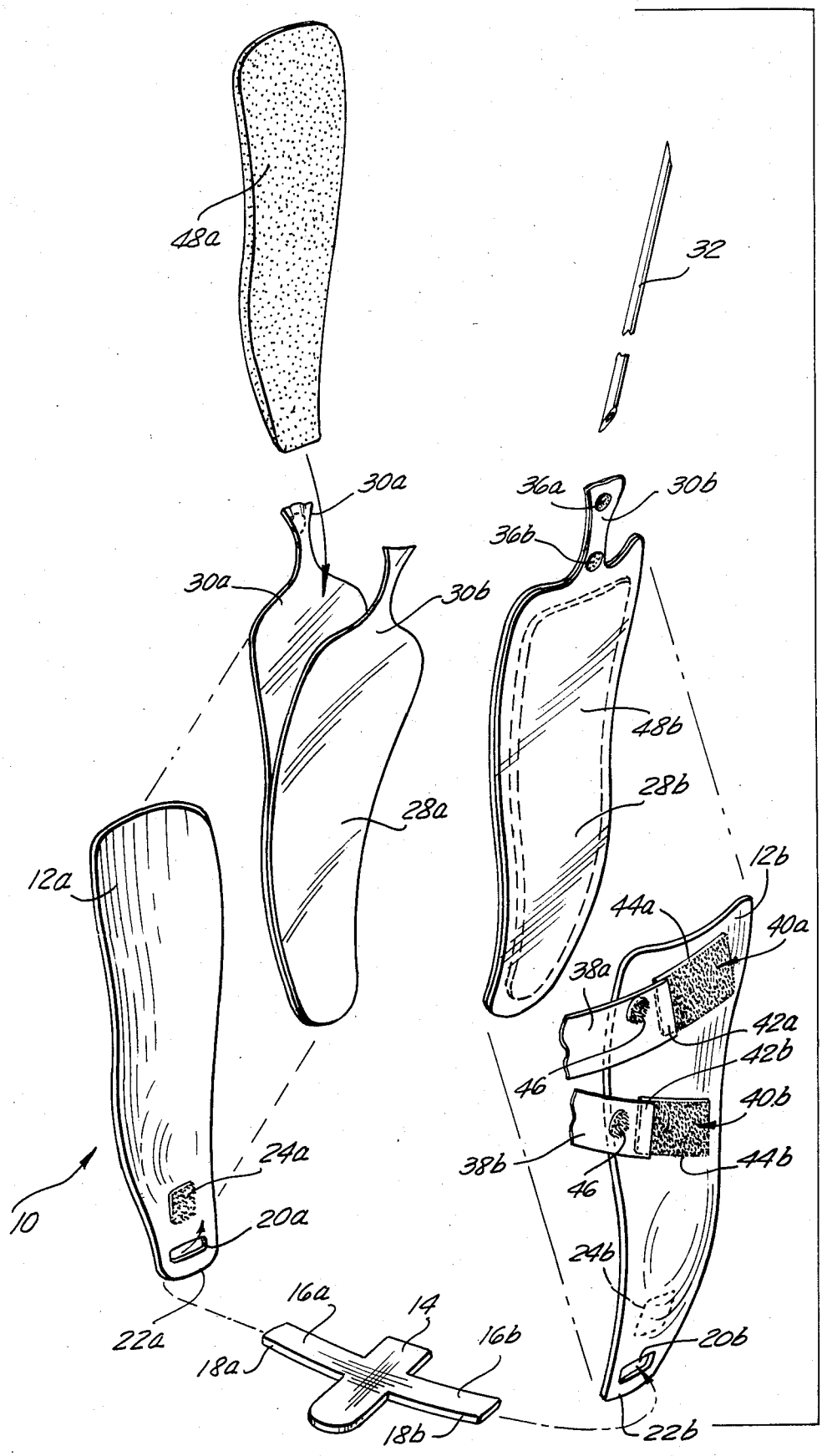
FIG. 1 is a diagramatic, exploded perspective view of the improved ankle brace of the present invention.

Turning initially to FIG. 1 there is diagramatically shown an ankle brace generally represented by reference numeral 10 which in its preferred form comprises a pair of outer shell members 12a, 12b preferably of a stiff, durable, molded plastic material generally shaped to conform to the lateral and medial sides of the lower extremity, respectively, and a base member 14 having a pair of oppositly extending, hinge portions 16a, 16b. Preferably, the base member 14 and hinge portions 16a, 16b are formed from a common piece of flexible woven nylon material cut to size and shaped substantially as shown and having bonded thereto a layer of fastener material such as that commonly sold under the VELCRO trademark.

Figure 2:
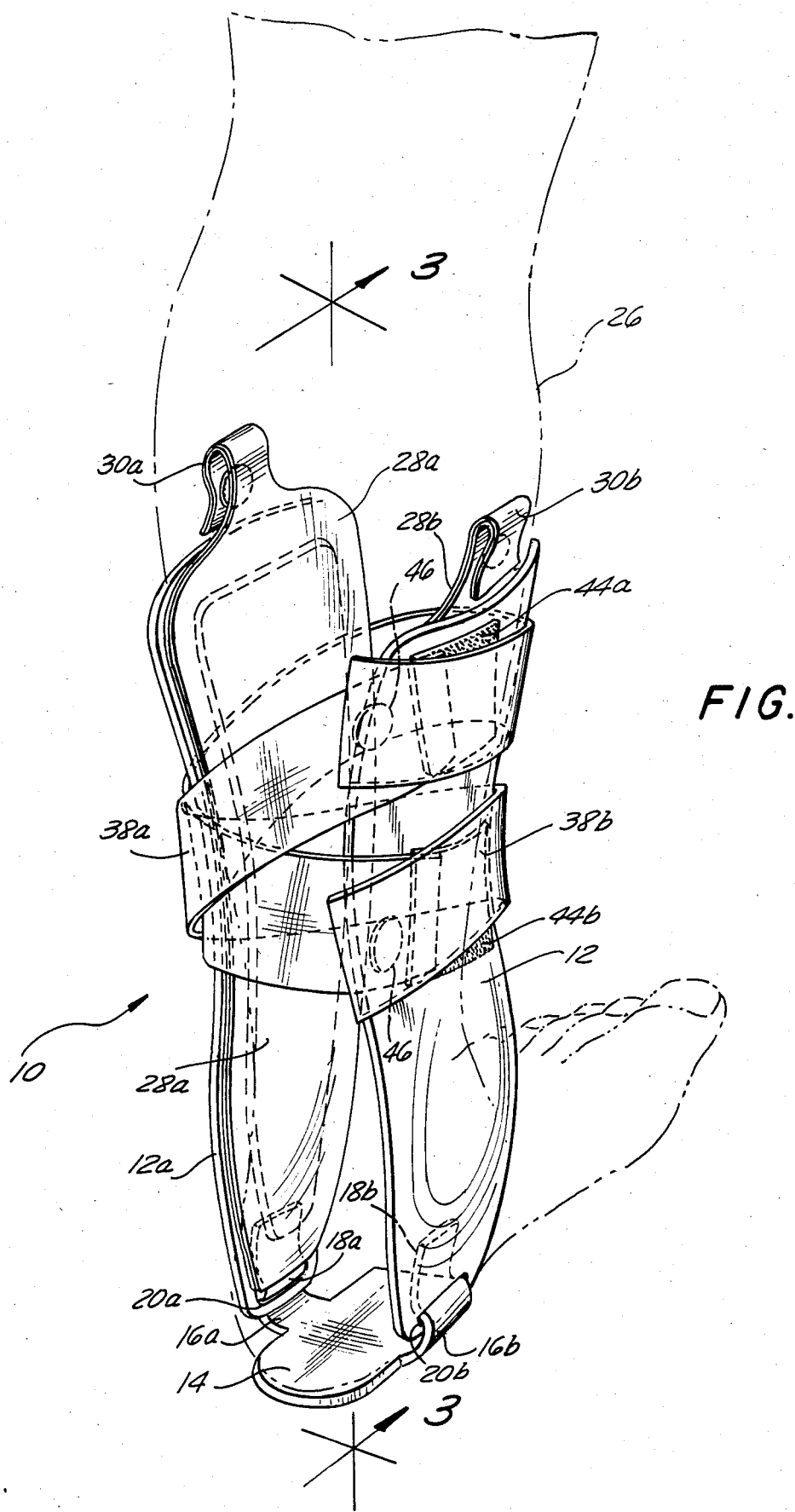
FIG. 2 is a diagramatic, perspective view showing the improved ankle brace of the present invention in assembled relation fitted about the lower extremity.

As best seen in FIGS. 2 and 3, the distal ends 18a, 18b of hinge portions 16a, 16b are adapted to be inserted through transverse slots 20a, 20b proximal to the lower edges 22a, 22b of shell members 12a, 12b and thereupon be fastened to a pair of mating VELCRO fastener patch elements 24a, 24b attached to the inside surface of the shell members 12a, 12b in slightly spaced relation above slots 20a, 20b, preferably by means of a suitable adhesive. It will be apparent that when the shell members and the base portion are so assembled, there is formed a U-shaped stirrup member adapted to be fitted about the lower extremity with the heel of the foot resting upon the base member and the shell members forming a pair of upwardly extending sidewall portions adapted to be flexed into confronting engagement with corresponding opposed side portions of the lower extremity substantially as depicted in FIGS. 2–4 with the lower extremity (i.e., the left leg, ankle, and foot of a human) being indicated schematically by broken line 26.

A pair of air-inflatable, flexible liners or airbags 28a, 28b are disposed, respectively, on the inwardly facing opposed surfaces of shell members 12a, 12b in a generally juxtaposed manner coextensive therewith. Each airbag 28a, 28b preferably is of the type more fully disclosed in my prior U.S. Pat. No. 4,287,920, entitled "Self Sealing Valve", which is hereby incorporated herein by this reference, and comprises a pair of thin sheets 30a, 30b of pliable material (e.g. vinyl plastic) bonded together along their confronting peripheries as by known heat sealing techniques, for example. Each airbag 28a, 28b further includes an integral valve 30a, 30b extending upwardly therefrom as generally shown in FIG. 1 for facilitating the selective inflation of airbags 28a, 28b by mouth entubation via flexible plastic tube 32 inserted into the throat of the valves 30a, 30b. The structural details of valves 30a, 30b are more fully described in the '920 patent and are outside the scope of the present invention. Suffice it to say, any conventional one-way valve for admitting and exhausting air to and from the interior of airbags 28a, 28b will be suitable. Airbags 28a, 28b are affixed to the opposed, inwardly facing surfaces of shell members 12a, 12b preferably using a conventional adhesive, so that each attached airbag extends coextensively over substantially the entire inner surface of its corresponding shell member with the integral valves 30a, 30b of the shell members extending above the upper edges 34a, 34b of the shell members, and with the lower distal extremity of the airbags overlapping the distal ends 18a, 18b of base member hinge portions 16a, 16b as seen to best advantage in FIGS. 2 and 3. If desired, each valve 30a, 30b may have fastened thereto a pair of spaced, mating VELCRO fasteners 36a, 36b to enable the valve to be folded down over itself and fastened in place (FIGS. 2 and 3) thereby presenting a neater appearance and helping to avoid leakage of air through each valve, respectively.

In order to maintain ankle brace 10 in proper fitting engagement about the lower extremity, a pair of elongate, longitudually spaced, circumferentially extending fastener straps 38a, 38b are provided (partially broken away in FIG. 1). Preferably, each strap 38a, 38b is fabricated of the same well known woven nylon material as base member 14 and therefore includes a layer of VELCRO fastening material on the underside thereof as viewed in FIGS. 1-3. A pair of VELCRO fastener patch elements 40a, 40b are attached to the outer surface of shell member 12b, preferably by means of a suitable adhesive, and are adapted to securely mate with the VELCRO fastening material on the underside of each strap member 38a, 38b. In the preferred arrangement one end of strap member 38a is thusly secured to the left-most portion 42a of mating fastener element 40a whereas one end of strap member 38b likewise is secured to the left-most portion 42b of mating fastener element 40b thereby permitting the other or distal ends of strap members 38a, 38b to be securely fastened to the right-most portions 44a, 44b of fastener patch elements when the strap members are circumferentially drawn and tensioned snuggly about the exterior of both shell members. If desired, additional VELCRO fastener elements 46 may be attached to the outer surface of strap members 38a, 38b to further matingly engage with and secure the free or other end thereof as shown in FIGS. 1 and 3. Likewise, additional VELCRO fastener elements similar to elements 46 (not shown) may be attached to the outer surface of shell member 12a to further matingly engage the portions of strap members 38a, 38b in circumferential contact therewith when the strap members are tightened and fastened about the shell members as will be described in more detail below.

Described thus far, ankle brace 10 generally is similar in overall organization to the ankle brace described in my prior U.S. Pat. No. 4,280,489, entitled "Ankle Brace", and also incorporated herein by this reference. In the patented device, the airbags are inflated exclusively with air preferably after the ankle brace is fitted about the lower extremity. In accordance with the present invention, however, means in the form of filler members or pads 48a, 48b are provided for pre-inflating airbags 28a, 28b during fabrication i.e., the filler member is inserted between the plies of its corresponding airbag before they are heat sealed together along their confronting peripheries. Each filler member 48a, 48b is shaped and sized to substantially completely fill the interior of its corresponding airbag, and is formed of a compressable, resilient material that is porous and permeable to air (i.e., sponge-like in character). The preferred filler material is open cell urethane foam which is widely commercially available, but any other suitable material having the foregoing characteristics will suffice e.g., sponge rubber.

Without limiting the present invention, I have found quite surprisingly that in an ankle brace having shell members approximately 10 inches in longitudional extent and 3.5 inches in transverse extent (maximum), a urethane pad having a substantially uniform thickness in the range of about 0.20 inches to about 0.24 inches, with 0.22 inches being particularly preferred, yields a filler member having a sufficient volume of entrapped air to obviate the need for additional or supplemental inflation of each airbag after the ankle brace is fitted about the lower extremity. The reason for this is fully apparent in FIGS. 3 and 4 which show the lower and upper portions of filler members 48a, 48b being compressed by protruding portions of the lower and upper extremity (i.e., the malleolus and the calf, respectively) when the ankle brace is in fitting engagement about the lower extremity. Such compression causes the air entrapped within the compressed portions of the filler member to displace into the central portion 50 of each airbag where relatively larger voids exist between the outer shell members and the lower extremity. Since the volume of air inside each airbag remains constant, the aforementioned compression causes the air pressure inside each airbag to increase thus creating the desired pressurized air layer in supporting engagement with the lower extremity i.e., a supporting pressure within the range of about 15 mm Hg. to about 25 mm Hg. Moreover, the filler members, despite being compressed, serve the dual function of simultaneously providing a protective cushion between the hard inner surface of each shell member and the protruding portions of the lower extremity thereby avoiding discomfort to the wearer. The foregoing synergistic result of obviating supplemental inflation of airbags 28a, 28b and simultaneously, providing a cushioning effect between the outer shell members and the protruding portions of the lower extremity is incapable of being accomplished by prior art ankle braces which fail to even remotely contemplate the use of the filler members 48a, 48b according to the present invention.

Furthermore, it will be appreciated that the provision of filler members 48a, 48b as disclosed in the present specification simplifies applying or fitting the ankle brace 10 about the lower extremity. Thus, after positioning the lower extremity between the shell members 12a, 12b with the heel of the foot resting upon base member 14, and putting on and lacing the shoe to be worn with the ankle brace, all that is necessary is to squeeze or flex the shell members toward each other with one hand until they are in snug supporting engagement with the ankle and lower leg, while with the other hand, each fastener strap 38a, 38b is circumferentially drawn and tensioned about both shell members until comfortable, but not excessive compression of the filler members is achieved. The fastener straps may then be fixedly secured in place via mating VELCRO fasteners 40a, 40b, and 46. If desired, a final adjustment for additional comfort or support may be achieved by further inflating one or both airbags 28a, 28b by inserting tube 32 into valves 30a, 30b and using mouth entubation. Similarly, the tube 32 and valve 30a, 30b may be used to relieve a build-up in excessive pressure in airbags 28a, 28b, as for example, when the ankle brace is worn aboard an airplane flying at elevated altitude. After such pressure relief is effected, straps 38a, 38b should be readjusted to once again achieve an optimum balance between comfort, compression of filler members 48a, 48b, and supporting pressure.

Finally, it will be observed that the width of base member 14 and the spacing between the shell members 12a, 12b may be adjusted to fit lower extremities of varying size by peeling back the lower portion of each airbag 28a, 28b, releasing the attachment between distal portions 18a, 18b of hinge portions 16a, 16b and VELCRO fasteners 24a, 24b, and reattaching as desired.

As used herein, the term "lower extremity" should be interpreted broadly to include the foot, the ankle, and the lower leg.

Obviously, many modifications and alterations of the present invention will occur to these with ordinary skill. Accordingly, the present invention should be limited only by the spirit and scope of the appended claims.

I claim:

1. Orthopedic apparatus comprising:
   a base portion,
   a pair of spaced apart sidewall portions hingedly attached to opposite sides of said base portion,
   a pair of support members disposed coextensively with respect to said sidewall portions on opposite sides of said base portion in a confronting manner with respect to each other, at least one of said support members comprising an inflatable bladder, said inflatable bladder comprising a pair of plies of flexible material joined to one another along their common peripheral extents, and
   compressible filler means in the form of a porous pad disposed interiorly within said inflatable bladder, said porous pad and the air entrapped therein serving as the primary means for inflating said inflatable bladder whereby compression of a portion of said bladder and a portion of said pad coextensive therewith in one region thereof causes air entrapped in said pad to displace to at least another region of said bladder remote from said one region to form a pressurized air layer within said bladder coextensive with said at least another region.

2. The apparatus of claim 1 further comprising valve means associated with said inflatable bladder for selectively admitting or exhausting air to or from the interior thereof.

3. The apparatus of claim 1 wherein said porous pad is open cell urethane foam.

4. The apparatus of claim 1 further comprising fastener strap means adapted to maintain said sidewall portions in engagement with the lateral and medial portions of the lower extremity.

5. The apparatus of claim 3 wherein said porous pad is of substantially uniform thickness in the range of about 0.20 inches to about 0.24 inches.

6. The apparatus of claim 1 further comprising hinge means on said base portion adjustably attached to the bottom portion of each of said sidewall portions to permit selective adjustment of the spacing of said sidewall portions relative to said base portion and to one another.

7. The apparatus of claim 1 wherein each of said pair of support members comprises an inflatable bladder.

8. The apparatus of claim 7 wherein separate compressible filler means in the form of a porous pad are disposed interiorly within each of said inflatable bladders, respectively.

9. The apparatus of claim 1 wherein said at least one inflatable bladder and its corresponding coextensive sidewall portion is shaped to conform to the side of the lower extremity in the vicinity of the malleolus such that compression of said bladder and said porous pad in said one region is caused by engagement therewith by said malleolus when said corresponding sidewall portion is hingedly displaced relative to said base portion, and said pressurized air layer coextensive with said at least another region extends into at least a portion of the voids formed between that part of the lower extremity proximal to the malleolus and said corresponding sidewall portion.

* * * * *